United States Patent 
Gray

(10) Patent No.: US 6,957,148 B2
(45) Date of Patent: Oct. 18, 2005

(54) NEXT-NEAREST-NEIGHBOR SEQUENCE DETERMINANTS OF ANTISENSE DNA

(75) Inventor: Donald M. Gray, Richardson, TX (US)

(73) Assignee: The Board of Regents, University of Texas System, Austin, TX (US)

( * ) Notice: Subject to any disclaimer, the term of this patent is extended or adjusted under 35 U.S.C. 154(b) by 93 days.

(21) Appl. No.: 10/151,277

(22) Filed: May 20, 2002

(65) Prior Publication Data

US 2003/0228577 A1 Dec. 11, 2003

Related U.S. Application Data

(60) Provisional application No. 60/292,501, filed on May 21, 2001.

(51) Int. Cl.⁷ .......................... G01N 33/48; G06F 19/00
(52) U.S. Cl. .......................................... 702/19; 702/20
(58) Field of Search ...................... 702/19, 20; 703/11; 435/6

(56) References Cited

U.S. PATENT DOCUMENTS

| 5,856,103 A | 1/1999 | Gray et al. ..................... 435/6 |
| 6,183,966 B1 | 2/2001 | Gray et al. ..................... 435/6 |

FOREIGN PATENT DOCUMENTS

| WO | WO 94/23755 A1 | 10/1994 |
| WO | WO 95/02069 A1 | 1/1995 |

OTHER PUBLICATIONS

Hidetoshi Arima, et al., "Design of Potent Phosphorothioate Antisense Oligonucleotides Directed to Human Interleukin 10 Gene Product and Their Evaluation of Antisense Activity in U937 Cells", Pharmaceutical Research (New York), vol. 16, (No. 8), pp. 1163–1171, 1999.

S.T. Crooke, "Basic Priniciples of Antisense Therapeutics", Antisense Research and Applications, CRC Press, GB, pp. 1–50, 1998.

Wen–Chun Hung, et al, "Antisense Oligodeoxynucleotides Targeted Against Different Regions of CyclinD1 mRNA May Exert Different Inhibitory Effects on Cell Growth and Gene Expression", Biochemical and Biophysical Research Communications, vol. 220,(No. 3), pp. 719–723, 1996.

Sergey V. Ivanov, et al., "Down–Regulation of Transmembrance Carbonic Anhydrases in Renal Cell Carcinoma Cell Lines by Wild–Type Von Hippel–Lindau Transgenes", Proceedings of the National Academy of Science of USA, vol. 95, pp. 12596–12601, 1998.

Song Hai–Feng, et al., "Application of Secondary Structure Prediction in Antisense Drug Design Targeting Protein Kinase C-α mRNA and QSAR Analysis", Acta Pharmacologica Sinica, vol. 21 (No. 1), pp. 80–86, 2000.

Masato Mitsuhashi, "Strategy for Designing Specific Antisense Oligonucleotide Sequences", Journal of Gastroenterology, vol. 32, (No. 2), pp. 282–287, 1997.

Alexey V. Laptev, et al., "Specific Inhibition of Expression of a Human Collagen Gene (COL1A1) with Modified Antisense Oligonucleotides. The Most Effective Target Sites Are Clustered in Double–Stranded Regions of the Predicted Secondary Structure for the mRNA ", Biochemistry, vol. 33 (No. 38), pp. 11033–11039, 1994.

Donald M. Gray and Ignacio Tinoco, Jr., "A New Approach to the Study of Sequence–Dependent Properties of Polynucleotides," Biopolymers, vol. 9, John Wiley & Sons, Inc., pp. 223–244, 1970.

Rosanne M. Orr and Brett P. Monia, "Antisense Therapy for Cancer", Current Research in Molecular Therapeutics, vol. 1 (No. 2), pp. 102–108, 1998.

Soumitra Basu and Eric Wickstrom, "Temperature and Salt Dependence of Higher Order Structure Formation by Antisense c–myc and c–myb Phosphorothioate Oligodeoxyribonucleotides Containing T traguanylate Tracts", Nucleic Acids Research, vol. 25 (No. 7), Oxford University Press, pp. 1327–1332, 1997.

Christian Beltinger, et al., "Binding, Uptake, and Intracellular Trafficking of Phosphorothioate–modified Oligodeoxynucleotides", J. Clin. Invest., vol. 95, The American Society for Clinical Investigation, Inc. pp. 1814–1823, 1995.

C. Frank Bennett, et al., "Inhibition of Endothelial C II Adh slon Molecule Expression with Antisense Oligonucleotides", Journal of Immunology, The American Association of Immunologists, pp. 3530–3540, 1994.

(Continued)

Primary Examiner—Marianne P. Allen
Assistant Examiner—Jerry Lin
(74) Attorney, Agent, or Firm—Locke Liddell & Sapp

(57) ABSTRACT

The use of antisense oligodeoxyribonucleotides (ODNs) to inhibit translation of mRNAs promises to be an important means of controlling gene expression and disease processes. ODNs are about 20 nucleotides long, so hundreds of possible targets are available in a given mRNA. An elusive goal has been to efficiently predict the best in vivo antisense target without having to study a large pool of possible ODN sequences for each mRNA. It would be a breakthrough if ODN selection could be accurately guided by the application of sequence specific parameters to an mRNA sequence. The selection of the best ODN sequence is complicated since cellular uptake, conditions at the mRNA target site, non-sequence-specific effects, sequence redundancy, and mRNA secondary structures are difficult to predict. Thermodynamic parameters for nearest-neighbor (dimer) duplex stabilities, from in vitro studies, have not been adequate predictors of in vivo hybridization. The methodology of this application shows that it is possible to obtain parameters for in vivo motifs, which are defined as combinations of next-nearest-neighbors, that are correlated with efficient antisense targeting. These parameters can be used to identify mRNA sequences that are binding sites for effective antisense ODNs. Next-nearest-neighbor nucleotide parameters can be derived directly from cell culture inhibition data so that in vivo conditions are taken into account.

21 Claims, 12 Drawing Sheets

OTHER PUBLICATIONS

Philip Bernstein, Research Briefs, This Month in Nature Biotechnology, vol. 16 (No. 10), pp. 893–894, 1998.

Dwaine A. Braasch and David R. Corey, "Novel Antisense and Peptide Nucleic Acid Strategies for Controlling Gen Expression", Biochemistry, vol. 41 (No. 14), The American Chemical Society, pp. 4503–4510, 2002.

Andrea D. Branch, "A Good Antisense Molecule Is Hard to Find", Talking Point, Elsevier Science Ltd., pp. 45–50, 1998.

Catherine L. Cioffi, et al., "Selective Inhibition of A-Raf and C-Raf mRNA Expression by Antisense Oligodeoxynucleotides in Rat Vascular Smooth Muscle Cells: Role of A-Raf and C-Raf in Serum–Induced Proliferation", Molecular Pharmacology, vol. 51, The American Society for Pharmacology and Experimental Therapeutics, pp. 383–389, 1997.

Nicholas M. Dean, et al., "Inhibition of Proetin Kinase C-α Expression in Human A549 Cells by Antisense Oligonucleotides Inhibits Induction of Intercellular Adhesion Molecule 1 (ICAM–1) mRNA by Phorbol Esters", The Journal of Biological Chemistry, vol. 269 (No. 23), The American Society for Biochemistry and Molecular Biology, Inc., pp. 16416–16424, 1994.

Fritz Eckstein, "Searching For The Ideal Partner", Nature Biotechnology, vol. 16, (No. 1) p. 24, 1998.

Fritz Eckstein, "Phosphorothioate Oligodeoxynucleotides: What Is Their Origin and What Is Unique About Them?", Antisense & Nucleic Acid Drug Development, vol. 10, Mary Ann Leibert, Inc., pp. 117–121, 2000.

R.V. Giles, et al., "Selecting Optimal Oligonucleotide Composition For Maximal Antisense Effect Following Streptoylsin O–Mediated Delivery into Human Leukaemia Cells", Nucleic Acids Research, vol. 26, (No. 7), Oxford Univesitry Press, pp. 1567–1575, 1998.

Donald M. Gray, "Derivation of Nearest–Neighbor Properties from Data on Nucleic Acid Oligomers. I. Simple Sets of Independent Sequences and the Influence of Absent Nearest Neighbors", Biopolymers, vol. 42, John Wiley & Sons, Inc., pp. 783–793, 1997.

Donald M. Gray, "Derivation of Nearest–Neighbor Properties From Data on Nucleic Acid Oligomers. II. Thermodynamic Parameters of DNA—RNA Hybrids and DNA Duplexes", Biopolymers, vol. 42, John Wiley & Sons, Inc., pp. 795–810, 1997.

Gary D. Gray, et al., "Transformed and Immortalized Cellular Uptake of Oligodeoxynucleoside Phosphorothioates, 3'–Alkylamino Oligodeoxynucleoties, 2'–O–Methyl Oligoribonucleotides, Oligodeoxynucleoside Methlylphosphomates, and Peptide Nucleic Acids", Biochemical Pharmacology, vol. 53, Elsevier Science, Inc., pp. 1465–1476, 1997.

Gihan M. Hasham, "Hybrid Oligomer Duplexes Formed With Phosphorothioate DNAs: CD Spectra and Melting Temperature of S–DNA–RNA Hybrids Are Sequence–Dependent but Consistent With Similar Heteronomous Conformations", Biochemistry, vol. 37, American Chemical Society, pp. 61–72, 1998.

Siew Peng Ho, et al., "Potent Antisense Oligonucleotides to the Human Multidrug Resistance–1 mRNA ARe Rationally Selected by Mapping RNA–Accessible Sites With Oligonucleotide Libraries", Nucleic Acids Research, vol. 24, (No. 10), Oxford University Press, pp. 1901–1907, 1996.

Siew Peng Ho, etal., "Mapping of RNA Accessibe Sites for Antisense Experiments With Oligonucleotide Libraries", Nature Biotechnology, vol. 16, pp. 59–63, 1998.

Su–Hwi Hung, et al., "Evidence From CD Spectra That d(purine)–r(pyrimidine) and r(purine)–d(pyrimidine) Hybrids are in Different Structural Classes", Nucleic Acids Research, vol. 22 (No. 20), Oxford University Press, pp. 4326–4334, 1994.

Elena A. Lesnik and Susan M. Freier, "Relative Thermodynamic Stability of DNA, RNA, and DNA:RNA Hybrid Duplexes: Relationship with Base Composition and Structure", Biotechnology, vol. 34, American Chemical Society, pp. 10807–10815, 1995.

David H. Mathews, et al., "Predicting Oligonucleotide Affinity to Nucleic Acid Targets", RNA, vol. 5, Cambridge University Press, pp. 1458–1469, 1999.

Olga Matveeva, et al., "Predicition of Antisense Oligonucleotide Efficacy by In Vitro Methods", Nature Biotechnology, vol. 16, pp. 1374–1375, 1998.

O.V. Matveeva, et al., "Identification of Sequence Motifs in Oligonucleotides Whose Presence is Correlated With Antisense Activity", Nucleic Acids Research, vol. 28 (No. 15), Oxford University Press, pp. 2862–2865, 2000.

Dan Mercola and Jack S. Cohen, "Antisense Approaches to Cancer Gene Therapy", Cancer Gene Therapy, vol. 2, (No. 1), pp. 47–59, 1995.

Masato Mitsuhashi, et al., "Oligonucleotide Probe Design—A New Approach", Nature, vol. 367, (No. 6465), pp. 759–761, 1994.

Brett P. Monia, et al., "Evaluation of 2'–Modified Oligonucleotides Containing 2'–Deoxy Gaps as Antisense Inhibitors of Gene Expression", The Journal of Biological Chemistry, vol. 268, (No. 19), The American Society for Biochemsitry and Molecular Biology, Inc., pp. 14514–14522, 1993.

William H. Press, et al., "Numerical Recipes in C", The Art of Scientific Computing, Second Edition, Cambridge University Press, pp. 59–70, 1998.

Richard W. Roberts and Donald M. Crothers, "Stability and Properties of Double and Triple Helices: Dramatic Effects of RNA or DNA Backbone Composition", Science, vol. 258, pp. 1463–1466, 1992.

Deborah L. Sokol, et al., "Real Time Detection of DNA–RNA Hybridization in Living Cells", Proc. Natl. Acad. Sci., vol. 95, (no. 20), Applied Biological Sciences, pp. 11538–11543, 1998.

Deborah L. Sokol and Alan M. Gewirtz, "Monitoring Antisense Oligodeoxynucleotide Activity in Hematopoietic Cells", A Companion to Methods in Enzymology, vol. 17, Academic Press, pp. 219–230, 1999.

C.A. Stein and Y.C. Cheng, "Antisense Oligonucleotides as Therapeutic Agents—Is the Bullet Really Magical?", Science, vol. 261, pp. 1004–1012, 1993.

C.A. Stein, "Keeping the Biotechnology of Antisense in Context", Nature Biotechnology, vol. 17, p. 209, 1999.

Robert A. Stull, "Predicting Antisense Oligonucleotide Inhibitory Efficacy: A Computational Approach Using Histograms and Thermodynamic Indices", Nucleic Acids Research, vol. 20, (No. 13), Oxford University Press, pp. 3501–3508, 1992.

Naoki Sugimoto, et al., "Thermodynamic Parameters To Predict Stability of RNA/DNA Hybrid Duplexes", Biochemistry, vol. 34, American Chemical Society, pp. 11211–11216, 1995.

Guang–Chou Tu, et al., "Tetranucleotide GGGA Motif in Primary RNA Transcripts", The Jouranl of Biological Chemistry, vol. 273, (No. 39), The American Society for Biochemistry and Molecular Biology, Inc., pp 25125–25131, 1998.

Richard W. Wagner and W. Michael Flanagan, "Antisense Technology and Prospects for Therapy of Viral Infections and Cancer", Molecular Medicine Today, pp. 31–38, 1997.

S. Patrick Walton, et a l., "Thermodynamic and Kinetic Characterization of Antisense Oligodeoxynucleotide Binding to a Structured mRNA", Biophysical Journal, vol. 82 (No. 1), pp. 366–377, 2002.

Mark D. Matteucci and Richard W. Wagner, "In Pursuit of Antisense", Nature, vol. 384 (6604 Suppl), pp. 20–22, 1996.

| | Fig. 2A |
|---|---|
| | Fig. 2B |
| | Fig. 2C |

Fig. 2

A matrix of dimensions 3 × 64 for three 20-mer mRNA sequences in C-Raf1 mRNA and the occurrence of the 64 possible next-nearest-neighbor triplets in the sequences. The sequences are considered to be closed circles, so each sequence has 20 NNN triplets.

mRNA sequence #85: 5'-GGCGGCCUGGCUCCCUCAGG-3'
mRNA sequence #130: 5'-AUGGAGCACAUACAGGGAGC-3'
mRNA sequence #707: 5'-UCUUAUUGUUCCAAAUUCC-3'

Matrix NNN triplets 1-16:

| mRNA Seq | 1 AAA | 2 AAU | 3 AAC | 4 AAG | 5 AUA | 6 AUU | 7 AUC | 8 AUG | 9 ACA | 10 ACU | 11 ACC | 12 ACG | 13 AGA | 14 AGU | 15 AGC | 16 AGG |
|---|---|---|---|---|---|---|---|---|---|---|---|---|---|---|---|---|
| #85 | 0 | 0 | 0 | 0 | 0 | 0 | 0 | 0 | 0 | 0 | 0 | 0 | 0 | 0 | 0 | 1 |
| #130 | 0 | 0 | 0 | 0 | 1 | 0 | 0 | 1 | 2 | 0 | 0 | 0 | 0 | 0 | 2 | 1 |
| #707 | 1 | 1 | 0 | 0 | 0 | 2 | 0 | 0 | 0 | 0 | 0 | 0 | 0 | 0 | 0 | 0 |

Fig. 2A

Matrix NNN triplets 17-32:

| 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| UAA | UAU | UAC | UAG | UUA | UUU | UUC | UUG | UCA | UCU | UCC | UCG | UGA | UGU | UGC | UGG |
| 0 | 0 | 0 | 0 | 0 | 0 | 0 | 0 | 1 | 0 | 1 | 0 | 0 | 0 | 0 | 1 |
| 0 | 0 | 1 | 0 | 0 | 0 | 0 | 0 | 0 | 0 | 0 | 0 | 0 | 0 | 0 | 1 |
| 0 | 1 | 0 | 1 | 1 | 1 | 2 | 1 | 0 | 1 | 2 | 0 | 0 | 1 | 0 | 0 |

Matrix NNN triplets 33-48:

| 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|
| CAA | CAU | CAC | CAG | CUA | CUU | CUC | CUG | CCA | CCU | CCC | CCG | CGA | CGU | CGC | CGG |
| 0 | 0 | 0 | 1 | 0 | 0 | 2 | 1 | 0 | 2 | 1 | 0 | 0 | 0 | 0 | 1 |
| 0 | 2 | 1 | 1 | 0 | 0 | 0 | 0 | 0 | 0 | 0 | 0 | 0 | 0 | 0 | 0 |
| 1 | 0 | 0 | 0 | 1 | 1 | 1 | 0 | 1 | 1 | 0 | 0 | 0 | 0 | 0 | 0 |

Fig. 2B

Matrix NNN triplets 49-64:

| | 49 | 50 | 51 | 52 | 53 | 54 | 55 | 56 | 57 | 58 | 59 | 60 | 61 | 62 | 63 | 64 |
|---|---|---|---|---|---|---|---|---|---|---|---|---|---|---|---|---|
| | GAA | GAU | GAC | GAG | GUA | GUU | GUC | GUG | GCA | GCU | GCC | GCG | GGA | GGU | GGC | GGG |
| | 0 | 0 | 0 | 0 | 0 | 0 | 0 | 0 | 0 | 1 | 1 | 1 | 0 | 0 | 3 | 2 |
| | 0 | 0 | 0 | 2 | 0 | 0 | 0 | 0 | 2 | 0 | 0 | 0 | 2 | 0 | 0 | 0 |
| | 0 | 0 | 0 | 0 | 0 | 1 | 0 | 0 | 0 | 0 | 0 | 0 | 0 | 0 | 0 | 1 |
| | 0 | 0 | 0 | 0 | 0 | 0 | 0 | 0 | 0 | 0 | 0 | 0 | 0 | 0 | 0 | 0 |

Fig. 2C

SEQUENCE LISTING

```
<160> NUMBER OF SEQ ID NOS: 3

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggcggccugg cucccucagg                                                     20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
auggagcaca uacagggagc                                                     20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucuuauuguu uccaaauucc                                                     20
```

NEXT-NEAREST-NEIGHBOR SEQUENCE DETERMINANTS OF ANTISENSE DNA

CROSS-REFERENCES TO RELATED APPLICATIONS

This Application for patent claims the benefit of priority from, and hereby incorporates by reference the entire disclosure of, co-pending U.S. Provisional Application for Pat. Ser. No. 60/292,501 filed May 21, 2001.

STATEMENT REGARDING PARTIAL PRIVATELY SPONSORED RESEARCH OR DEVELOPMENT

The development of this invention was funded in part by Grant No. 009741-0021-1999 from the Texas Higher Education Coordinating Board and a grant from eXegenics, Inc.

TECHNICAL FIELD OF INVENTION

The present invention relates generally to the field of antisense gene therapy and methods for identifying therapeutic oligodeoxyribonucleotides (ODNs) with the most suitable sequences for regulation of pathogenic processes associated with specific genetic diseases and for identifying oligodeoxyribonucleotides for the general control of gene expression, whether or not the gene is involved in a known genetic disorder.

BACKGROUND OF THE INVENTION

The field of antisense therapy involves techniques that attempt to treat a variety of disorders that are associated with genetic deficiencies or defects. One type of gene therapy treatment takes the form of treating the patient with a regulatory molecule, such as an antisense DNA oligodeoxyribonucleotide (ODN) molecule that binds to messenger RNA (mRNA) with the subsequent inhibition or control of translation and, hence, control of the production of a protein product. The antisense molecule is typically an oligonucleotide modified so as to have a long lifetime in the presence of cellular nucleases as well as to have high efficiency in hybridization to the target mRNA or genomic DNA. However, these modifications can result in undesirable side effects, one of which is that the ODN binds to cellular proteins and inhibits cellular functions in unpredictable ways [Mercola & Cohen, 1995; Orr & Monia 1998; Eckstein 2000][1]. FIG. 1 illustrates the fact that the desired effect of an antisense ODN requires that the ODN reach the target mRNA in the cellular nucleus and that the ODN be able to selectively bind to a region (typically 20 nucleotides long) of the target mRNA, but not to other mRNAs. Non-specific binding to cellular proteins on the cell surface, in the cytoplasm, or in other compartments, including the nucleus, can reduce effective ODN concentrations. Therefore, the antisense effect in vivo is dependent on many factors.

[1] All of the references cited herein and provided in the disclosed Bibliography are fully incorporated by reference in the specification.

Antisense oligodeoxyribonucleotides (ODNs), typically designed to be complementary to a specific mRNA target sequence of about 20 nucleotides, have been shown to be effective as a means of transient disruption of gene expression at the translational level [Sokol et al., 1998; Sokol & Gewirtz, 1999]. Thirteen antisense ODNs, six of which are targeted to cancer genes, are approved or are in clinical trials [Braasch & Corey, 2002]. The first generation of antisense drugs consists of phosphorothioate-modified oligodeoxyribonucleotides (S-ODNs), in which one of the non-bridging oxygens is replaced by sulfur to inhibit nuclease degradation. S-ODNs, like unmodified DNA, exert their effect mainly by activating RNAse H, which binds to the sites of S-ODN:mRNA hybridization and cleaves the mRNA. There is growing evidence that this antisense effect takes place in the nucleus, although the uptake mechanism and nuclear localization can depend on ODN concentration [Beltinger et al., 1995; Gray et al., 1997; Orr & Monia, 1998; Sokol & Gewirtz, 1999]. Methods are now available to correlate ODN:mRNA hybridization with a reduction in mRNA and protein levels [Sokol et al., 1998; Sokol & Gewitz, 1999].

S-ODNs can exert a true antisense inhibition of translation, which is sequence-specific, as exemplified in studies of C-raf and A-raf inhibition by S-ODNs with increasing numbers of mismatches [Coiffi et al., 1997]. However, a plethora of effects, broadly denoted as non-specific, compromise the ability to predict true sequence-specific antisense effects on the basis of in vitro hybridization data [Branch, 1998; Stein, 1999]. These non-specific effects include the competing secondary structures of mRNA target sites, partial complementarity of ODNs with unintended sites, the interactions of ODNs with intracellular and extracellular proteins, ODN self-structures such as G-quartet structures (although G-containing tetraplex structures may not form under intracellular conditions [Basu & Wickstrom, 1997]), effects of carriers, the cell type, the particular mRNA that is targeted, and conditions at the mRNA target site. Moreover, cellular delivery and subcellular trafficking may be somewhat sequence specific [Stein & Cheng, 1993; Wagner & Flanagan, 1997]. The type of ODN modification is also important. Chemical modifications other than phosphorothioate modification, such as 2'-O-alkyl and 2'-O-methoxyethoxy modifications, methylphosphonation, and 2'-5' linkage of 3'-deoxyribonucleotides, have been used to increase the stability and reduce the non-specific effects of antisense S-ODNs [Monia et al., 1993; Gray et al., 1997; Giles et al., 1998]. However, these modifications reduce RNase H sensitivity. For this reason, chimeric antisense ODNs that combine such modifications together with five to seven simple phosphorothioate nucleotides (to retain RNase H sensitivity) have been advocated [Monia et al., 1993]. Phosphorothioate modification thus remains an important modification.

Non-specific effects are not necessarily bad if they offer an added source of drug potency [Branch, 1998]. However, non-specific effects of ODN sequences have been difficult to predict, and a bottleneck remaining in the design of antisense drugs is the inability to make rational, a priori, selections of the best mRNA target sequences [Branch, 1998; Bernstein, 1998; Eckstein, 1998]. Others in the field are moving toward streamlined testing of all possible accessible sites on a target mRNA [Eckstein, 1998; Ho et al., 1998; Matveeva et al., 1998].

SUMMARY OF THE INVENTION

The present invention proposes a different approach to take account of many non-specific effects and enhance the ability to rationally identify potential antisense target sites. The method of the present invention is to derive, directly from in vivo data, a sequence-dependent set of parameters that is correlated with the antisense effect and that can be used to aid selection of mRNA target sites. Previously, parameters from in vitro studies have been used. Because in vitro studies of oligomer duplexes have shown that thermodynamic stability can be described as a property of the nearest-neighbor (NN) base pairs, the simplest premise has been that NN stabilities might dominate the sequence-dependent antisense effect. All 16 distinguishable NN stabilities for DNA:RNA hybrids must be considered [Stull et al., 1992; Roberts & Crothers, 1992; Hung et al., 1994; Lesnik & Freier, 1995; Gray, 1997a; Gray, 1997b; Hashem et al., 1998; Ho et al., 1998]. For example, hybrids with adjacent purines in the RNA strand (e.g. r[AG]/d[CT]) are much more stable than those with adjacent pyrimidines in the RNA strand (e.g. r[CU]/d[AG]). Using published DNA:RNA hybrid stability data [Gray, 1997a; Gray, 1997b; Sugimoto et al., 1995], it is possible to calculate the theoretical variation in the free energy $\Delta G°$ (at 37° C., 1 M $Na^+$) for hybridizations of ODNs to all target sequences in an mRNA. Differences in the stabilities of DNA:mRNA sequences, based on stabilities of the NN base pairs obtained from in vitro thermodynamic measurements of paired oligomer hybrids, have been widely used as an important factor in the design of antisense ODN sequences and in the assessment of differences in the antisense effectiveness of ODNs targeted to different regions of the same mRNA [Stull et al., 1992; Mathews et al., 1999; Gray & Clark, 1999; Gray & Clark, 2001; Walton et al., 2002]. The NN hybrid stabilities, while important, are generally supplemented in predictive programs with other criteria, such as the stability of competing intrastrand mRNA base pairs that must be broken to allow ODN:mRNA pairing [Mathews et al., 1999; Walton et al., 2002]. However, even then, such predictions are of limited accuracy, and methods based on in vitro criteria cannot account for sequence-dependent in vivo effects as described in the previous section.

Although NN data are not highly predictive of antisense effectiveness, this does not mean that data for longer sequences, or data obtained under cellular conditions, would also be poor predictors. In an important survey, Tu et al. (1998) found that fewer than 42 of 2026 reports involved testing more than 10 ODN sequences before concluding that there was an antisense effect. From a further analysis of 42 effective antisense sequences (including those used in clinical trials), Tu et al. (1998) discovered that 20 of these were targeted to a GGGA motif in the mRNA. In other work, Matveeva et al. (2000) reported that GUGG, GGGA, GAGU, UGGC, and AGAG target motifs were positively correlated with antisense effectiveness, while CCCC, CAGU, UUA, CCGG, and UUU were negatively correlated with antisense effectiveness in a search of >1000 experiments. The method provided by the present invention allows the identification of a more comprehensive, discrete number of motifs of overlapping triplet sequence combinations and provides an unambiguous way to rank all possible sequences in terms of the antisense effectiveness of the motifs they contain.

Specifically, the present invention provides a method for designating a nucleotide sequence composed of 20 nucleotides as 20 next-nearest-neighbor nucleotide triplets. Such method is comprised of the following operations: treating the nucleotide sequence composed of 20 nucleotides as a closed sequence, with the ends of said sequence meeting to form a circle, reading the sequence three nucleotides at a time, moving up one nucleotide along the sequence, then reading the next three nucleotides, for 20 steps, and interpreting the 20 readings of three nucleotides each as being equal to 20 next-nearest-neighbor nucleotide triplets.

The present invention also provides a method for designating a nucleotide sequence of n nucleotides as n next-nearest-neighbor nucleotide triplets. Such method comprises the following: treating the n nucleotide sequence as a closed sequence, with the ends of said sequence meeting to form a circle, reading the nucleotide sequence three nucleotides at a time, moving up one nucleotide along the sequence, then reading the next three nucleotides, for n steps, and interpreting the n readings of three nucleotides each as being equal to n next-nearest-neighbor nucleotide triplets.

Additionally, the present invention provides a method for assigning parameters of antisense effectiveness to 64 next-nearest-neighbor nucleotide triplets from measurements of the antisense effectiveness of at least 64 nucleotide sequences, wherein the sequences are considered to be closed sequences without end effects. This method of the present invention is comprised of operations including the step of constructing a matrix X having N rows and M columns, wherein said matrix X has one row for each of a minimum of N=64 nucleotide sequences and one column for each of the possible M=64 types of next-nearest-neighbor nucleotide triplets for sequences containing the common four nucleotides, A, U, G, and C, and wherein the numbers in the matrix columns are the numbers of each type of next-nearest-neighbor nucleotide triplet in the sequence in the given row. Said method further comprises the steps of constructing a matrix Y with N rows and 1 column, wherein the numbers in the rows are measured values for the biological antisense effectiveness of the N sequences, dividing the rows of matrices X and Y by the respective errors in the measured values, constructing a matrix P having M rows and 1 column, wherein the numbers in the rows are the 64 parameters of antisense effectiveness assigned to the next-nearest-neighbor nucleotide triplets, checking that the matrices satisfy the condition that X multiplied by P equals Y, via matrix multiplication, and solving equation X multiplied by P equals Y via the singular value decomposition method, wherein said equation is solved for P. In one embodiment of the present invention, the measurements of antisense effectiveness for this method are taken from a database of in vitro measurements. In another embodiment of the present invention, the measurements of antisense effectiveness for this method are from a database of in vivo measurements.

The method of the present invention for assigning parameters of antisense effectiveness to 64 next-nearest-neighbor nucleotide triplets from measurements of antisense effectiveness is further defined wherein the measurements of antisense effectiveness are taken from a database of antisense effects with sequences of phosphorothioate oligonucleotides. In a preferred embodiment of the present invention, such measurements of antisense effectiveness are taken from a database of antisense effectiveness with sequences of chemical moieties that pair with an mRNA sequence in complementary fashion. In yet another embodiment of the present invention, said parameters for said 64 next-nearest-neighbor nucleotide triplets are effective in determining the antisense effectiveness of a phosphorothioate oligonucleotide of about 20 nucleotides in length. In one embodiment of the present invention, said parameters for said 64 next-nearest-neighbor nucleotide triplets, which are effective in determining the antisense effectiveness of a phosphorothioate oligonucleotide of about 20 nucleotides in length, are multiplied by L/20 for an oligonucleotide which is L nucleotides long.

In the present invention, the parameters for said 64 next-nearest-neighbor nucleotide triplets are effective in determining the antisense effectiveness of sequences of chemical moieties that pair with an mRNA sequence in complementary fashion for a length of about 20 nucleotides. The present invention further provides that said parameters for said 64 next-nearest-neighbor nucleotide triplets, which are effective in determining the antisense effectiveness of sequences of chemical moieties that pair with an mRNA sequence in complementary fashion for a length of about 20 nucleotides, are multiplied by L/20 for an oligonucleotide which is L nucleotides long.

An embodiment of the present invention also exists wherein the parameters for 64 next-nearest-neighbor nucleotide triplets are combined to give parameters for 49 independent combinations of next-nearest-neighbor nucleotide triplets. Moreover, additional parameters are to be included to specify type of organism, type of cell line, type of gene mRNA, or type of chemically-modified oligomer.

The present invention further provides a method for assigning parameters to 49 combinations of next-nearest-neighbor nucleotide triplets from measurements of the antisense effectiveness of at least 49 sequences, wherein the sequences are considered to be closed sequences without end effects. Such method is comprised of operations including the constructing of a matrix X having N rows and M columns, wherein said matrix X has one row for each of a minimum of N=49 nucleotide sequences and there is one column for each of the possible M=49 independent combinations of next-nearest-neighbor nucleotide triplets for sequences containing the common four nucleotides A, U, G, and C, wherein the numbers in the matrix columns are the numbers of each type of independent next-nearest-neighbor nucleotide combination in the sequence in the given row. Said method further comprises the operations of constructing a matrix Y having N rows and 1 column, wherein the numbers in the rows are the measured values for the biological antisense effectiveness of the N sequences, dividing the rows of matrices X and Y by the respective errors in the measured values, constructing a matrix P having M rows and 1 column, wherein the numbers in the rows are the 49 parameters of antisense effectiveness assigned to the independent next-nearest-neighbor nucleotide combinations, checking that the matrices satisfy the condition that X multiplied by P equals Y, via matrix multiplication, and solving the equation X multiplied by P equals Y via the singular value decomposition method, wherein said equation is solved for P.

In a preferred embodiment of the present invention, the measurements of antisense effectiveness for this method are taken from a database of in vitro measurements. In another preferred embodiment of the invention, the measurements of antisense effectiveness for this method are taken from a database of in vivo measurements. Said method provides that said measurements of antisense effectiveness are taken from a database of antisense effects with sequences of phosphorothioate oligonucleotides. In addition, the present invention provides that said measurements of antisense effectiveness are taken from a database of antisense effectiveness with sequences of chemical moieties that pair with an mRNA sequence in complementary fashion. The invention further provides that the parameters for said 49 combinations of next-nearest-neighbor nucleotide triplets are effective in determining the antisense effectiveness of a phosphorothioate oligonucleotide of about 20 nucleotides in length, wherein said parameters for said 49 combinations of next-nearest-neighbor nucleotide triplets are multiplied by L/20 for an oligonucleotide which is L nucleotides long.

Under the method of the present invention, the parameters for the 49 combinations of next-nearest-neighbor nucleotide triplets are effective in determining the antisense effectiveness of sequences of chemical moieties that pair with an mRNA sequence in complementary fashion for a length of about 20 nucleotides, wherein said parameters for said 49 combinations of next-nearest-neighbor nucleotide triplets are multiplied by L/20 for an oligonucleotide which is L nucleotides long. The invention provides that, in assigning parameters to 49 combinations of next-nearest-neighbor nucleotide triplets, additional parameters are to be included to specify type of organism, type of cell line, type of gene mRNA, or type of chemically-modified oligomer.

Sequence motifs longer than the nearest-neighbors have not been searched for in a comprehensive manner, and they have never been rigorously searched for using in vivo databases. The present invention provides a method for (1) identifying next-nearest-neighbor (NNN) triplet combinations as an objective description of motifs that describe antisense effectiveness and (2) using next-nearest-neighbor parameters to identify antisense targets on mRNAs. This method takes advantage of the fact that many of the factors that determine in vivo sequence-dependence antisense effectiveness are similar for various situations. Therefore, the detailed description that follows below is based on a limited set of data. From the following description, it will be recognized by those skilled in the art that NNN combinations can eventually be derived from a larger database that will allow discovery and comparisons of antisense-affiliated motifs in different genes, in different regions (coding, noncoding) of genes, for different cell lines, and for different ODN modifications.

BRIEF DESCRIPTION OF THE DRAWINGS

FIGS. 2A, 2B, and 2C Illustrations of a 3×64 matrix showing how three 20-mer sequences (SEQ ID NOS 1, 2 and 3, respectively in order of appearance) can be represented in terms of their next-nearest-neighbor triplet compositions. Each sequence is considered to be a closed circle, so that it has 20 NNN triplets.

DETAILED DESCRIPTION OF THE INVENTION

Figure 1:
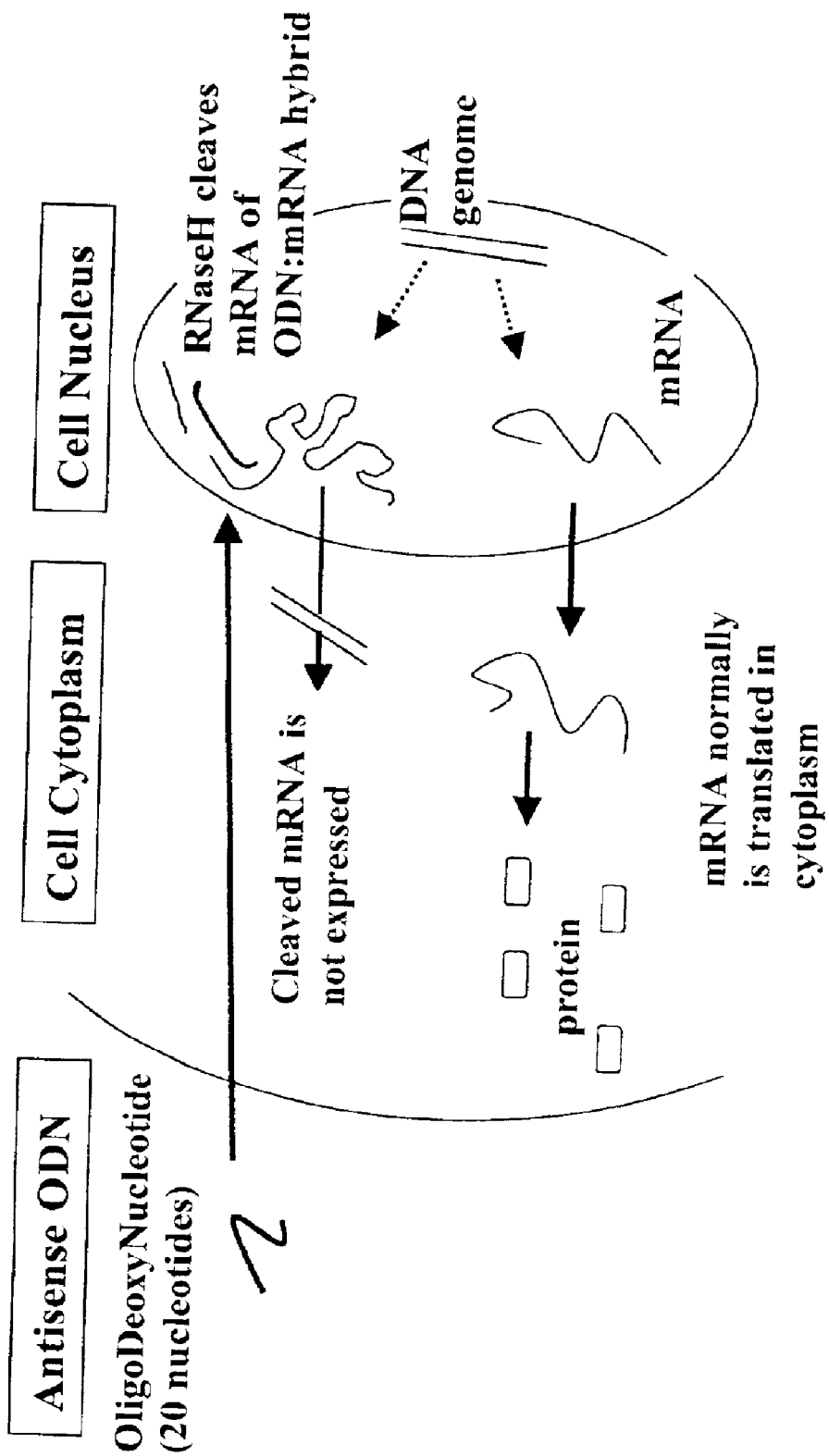
FIG. 1. A schematic illustration depicting antisense control of gene expression. To achieve an inhibitory effect on the expression of a particular gene product, the antisense ODN sequence must reach the cellular nucleus and bind to a complementary sequence on the mRNA transcript, whereby the mRNA is cleaved by an endogenous RNAse H enzyme. The cleaved mRNA is thus rendered ineffective as a template for protein synthesis in the cytoplasm.

The present invention involves the following operations:

(1) A database of antisense effects must be obtained for a number of sequences that is greater than the number of next-nearest-neighbor parameters that need to be determined. The database must have at least one example of each NNN triplet in at least one sequence. The method of the present invention is unique in that the database may consist of data obtained for in vivo antisense effects, but those skilled in the art will realize that other databases may be used to determine NNN parameters.

From our published theory [Gray, 1997a; Gray 1997b], if end effects are significant, 84 NNN parameters are needed to describe an array of sequence-dependent data for short oligomers. In the case of relatively long ODNs of 20-nucleotides, one can treat the sequences as closed sequences with no ends, which reduces the number of independent parameters to 49 [Gray, 1997a; Gray 1997b]. In this latter case, there are fewer than 64 (=$4^3$) NNN parameters because there are 15 constraints on arranging triplets in a closed sequence. A search of the literature and 42 references from Tu et al. (1998), revealed no single database large enough for such an analysis. In addition, only a few data sets of 20 or more included individual errors, which are needed to weight the % inhibition values for a singular value decomposition (SVD) analysis. In the present invention, data were obtained for a total of 102 antisense ODN sequences that contained representative numbers of all 64 NNN triplets. The ODNs were uniformly modified to contain phosphorothioate linkages between each nucleotide, with no phosphate groups at either end. Four gene products were targeted: C-Raf1, AKT2, Bcl-2, and PKCα, and the data was obtained from antisense treatments of two cell lines, T24 bladder cancer cells and A549 lung cancer cells. The specific sequence positions on the mRNAs and the inhibition data of protein levels are given in Table 1.

TABLE 1

Inhibition of protein levels from four genes when treated with 76 different phosophorothioate ODNs. Since 26 of the ODNs were used to treat two different cell lines for C-Raf1 inhibition, the total number of data points was 102.*

| Gene | Sequence starting position in mRNA of 20-mer target | % Inhibition of protein level in T24 cell line | Error (%)** | % Inhibition of protein level in A549 cell line | Error (%)** |
|---|---|---|---|---|---|
| C-Rail | 1 | 36.7 | 9.7 | 26.4 | *** |
|  | 41 | 46.8 | 4.6 | 47.7 | *** |
|  | 61 | 53.3 | 13.5 | 29.9 | *** |
|  | 85 | 39 | 15.9 | 40.8 | 9.70 |
|  | 121 | 53.3 | 1.3 | 50.1 | *** |
|  | 130 | 32.9 | 11.5 | 42.9 | 9.80 |
|  | 181 | 37.1 | 2.9 | 45.3 | *** |
|  | 301 | 34 | *** | 31.9 | *** |
|  | 361 | 39 | *** | 38.2 | *** |
|  | 707 | 34.5 | 12.6 | 22.1 | 10.90 |
|  | 761 | 29.4 | 6.6 | 44.5 | 9.80 |
|  | 821 | 43.1 | 7.4 | 51.2 | 10.10 |
|  | 1041 | 36.2 | 11.3 | 48.3 | 0.90 |
|  | 1063 | 47.6 | 18.5 | 48.6 | 10.70 |
|  | 1181 | 57.1 | 0.3 | 54.3 | 10.10 |
|  | 1474 | 48 | 12.3 | 51.7 | 7.40 |
|  | 1777 | 39.7 | 13.2 | 51.7 | 10.80 |
|  | 1867 | 42.5 | 10.5 | 55.5 | 5.50 |
|  | 2098 | 45 | 12.2 | 45.8 | 12.40 |
|  | 2341 | 66.1 | 25.2 | 59.9 | 0.30 |
|  | 2349 | 35.9 | 10.8 | 36.9 | 11.30 |
|  | 2484 | 59.2 | 20.1 | 52.4 | 4.80 |
|  | 2581 | 56.7 | 14.5 | 63 | 2.80 |
|  | 2601 | 24 | 2.4 | 42.1 | 12.70 |
|  | 2661 | 42.3 | 8.7 | 66.3 | 0.00 |
|  | 2681 | 42 | 1.8 | 49.2 | 4.10 |
| AKT2 | 57 |  |  | 41 | 14.00 |
|  | 86 |  |  | 54 | 5.00 |
|  | 94 |  |  | 46 | 6.00 |
|  | 490 |  |  | 58 | 7.00 |
|  | 973 |  |  | 55 | 9.00 |
|  | 1188 |  |  | 28 | 13.00 |
|  | 1227 |  |  | 41 | 17.00 |
| Bcl-2 | 23 |  |  | 41 | 14.00 |
|  | 36 |  |  | 54 | 5.00 |
|  | 61 |  |  | 46 | 6.00 |
|  | 109 |  |  | 58 | 7.00 |
|  | 120 |  |  | 55 | 9.00 |
|  | 201 |  |  | 28 | 13.00 |
|  | 277 |  |  | 41 | 17.00 |
|  | 316 |  |  | 51 | 6.00 |
|  | 361 |  |  | 30 | 14.00 |
|  | 409 |  |  | 46 | 8.00 |
|  | 445 |  |  | 53 | 8.00 |
|  | 453 |  |  | 45 | 3.00 |

TABLE 1-continued

Inhibition of protein levels from four genes when treated with 76 different phosophorothioate ODNs. Since 26 of the ODNs were used to treat two different cell lines for C-Raf1 inhibition, the total number of data points was 102.*

| Gene | Sequence starting position in mRNA of 20-mer target | % Inhibition of protein level in T24 cell line | Error (%)** | % Inhibition of protein level in A549 cell line | Error (%)** |
|---|---|---|---|---|---|
|  | 501 |  |  | 35 | 9.00 |
|  | 541 |  |  | 34 | 12.00 |
|  | 601 |  |  | 28 | 11.00 |
|  | 1041 |  |  | 50 | 5.00 |
|  | 1421 |  |  | 53 | 8.00 |
|  | 1481 |  |  | 56 | 5.00 |
|  | 1641 |  |  | 49 | 10.00 |
|  | 1761 |  |  | 52 | 5.00 |
|  | 1821 |  |  | 28 | 10.00 |
|  | 1941 |  |  | 50 | 10.00 |
|  | 2081 |  |  | 43 | 10.00 |
|  | 3101 |  |  | 37 | 6.00 |
|  | 3921 |  |  | 41 | 6.00 |
|  | 3941 |  |  | 43 | 4.00 |
|  | 3961 |  |  | 42 | 6.00 |
|  | 4881 |  |  | 44 | 7.00 |
|  | 5321 |  |  | 45 | 4.00 |
| PKCα | 121 | 42.0 | 9.0 |  |  |
|  | 281 | 49.5 | 9.8 |  |  |
|  | 288 | 51.0 | 1.0 |  |  |
|  | 301 | 22.0 | 9.0 |  |  |
|  | 321 | 24.0 | 2.0 |  |  |
|  | 341 | 29.0 | 4.0 |  |  |
|  | 421 | 16.7 | 17.6 |  |  |
|  | 441 | 18.6 | 10.2 |  |  |
|  | 481 | 11.0 | 3.0 |  |  |
|  | 501 | 53.0 | 7.0 |  |  |
|  | 541 | 15.0 | 1.0 |  |  |
|  | 621 | 22.8 | 11.3 |  |  |
|  | 899 | 62.6 | 3.9 |  |  |
|  | 2044 | 51.3 | 6.8 |  |  |

*From a preliminary NNN fit by SVD, the % inhibition data for five additional S-ODNs targeted to C-Raf1 mRNA had squared deviations of twice the average and were omitted from the final set.
**Errors are ranges from duplicate Western blots or standard deviations from three or more measurements
***Where no error is shown, the data are from single measurements and for the purpose of SVD analysis a maximum error of 15% was assumed.

(2) Each of the target mRNA sequences is separated into its constituent NNN triplets. This is illustrated in FIGS. 2A, 2B, and 2C for three of the target sequences in C-Raf1 mRNA. The total number of NNN triplets is 20 for each sequence, but, in general, they are different for each sequence. The array shown in FIGS. 2A, 2B, and 2C makes a 3×64 matrix. An additional row is added for each additional sequence. Additional columns in the matrix may be added to allow for differences in the data sets for different genes or cell lines or any other parameter than one wants to distinguish. For example, we added a 65th column with a "0" for every sequence that was used to inhibit the level of a gene product in T24 cells and a "1" for every sequence that was used to inhibit the level of a gene product in A549 cells. For the sequences in Table 1, the resulting matrix was 102 (# of sequences)×65 (# of parameters).

(3) Solve the matrix equation. The matrix equation $NNN_{hk} \times P_k = I_h$, where the NNN matrix has dimensions of h=102 and k=65, the P vector has k=65 values, one for each of the 64 NNN triplexes and one for the cell line, and I is the vector of % inhibition values for each sequence. Each hth row of the $NNN_{hk}$ matrix and the hth value of the $I_h$ vector is divided by the error for the hth sequence. This equation was solved as in our other work (Gray 1997b) using standard procedures (Press et al., 1992) to give values for the 65 parameters of the P vector and, hence, for the 49 independent combinations of the NNN triplets. The values for these parameters are listed in Table 2 for our specific data set. Those skilled in the art will realize that other sets of P parameters may be obtained for other data sets by the same procedure.

TABLE 2

Solution for the parameters P obtained from an SVD solution to fit the inhibitory data for 102 antisense sequences targeted to four gene mRNAs in two cell lines.

| Next-Nearest-Neighbor Triplet | Antisense inhibitory parameter from fit to 102 sequences | Number of NNN Triplet in Data Set |
|---|---|---|
| AAA | 8.323 | 25 |
| AAU | −6.973 | 27 |
| AAC | 6.819 | 24 |
| AAG | 0.455 | 33 |
| AUA | −4.545 | 15 |
| AUU | 1.258 | 20 |
| AUC | 1.728 | 16 |
| AUG | 0.872 | 64 |
| ACA | −5.736 | 41 |

TABLE 2-continued

Solution for the parameters P obtained from an SVD solution to fit the inhibitory data for 102 antisense sequences targeted to four gene mRNAs in two cell lines.

| Next-Nearest-Neighbor Triplet | Antisense inhibitory parameter from fit to 102 sequences | Number of NNN Triplet in Data Set |
|---|---|---|
| ACU | 3.613 | 28 |
| AGC | 5.101 | 21 |
| ACG | 4.638 | 25 |
| AGA | 2.685 | 36 |
| AGU | −3.902 | 11 |
| AGC | 0.196 | 38 |
| AGG | 8.428 | 50 |
| UAA | −3.399 | 6 |
| UAU | −6.522 | 16 |
| UAG | 1.179 | 15 |
| UAG | 11.364 | 8 |
| UUA | −1.557 | 9 |
| UUU | −3.087 | 22 |
| UUC | 0.294 | 22 |
| UUG | 6.464 | 27 |
| UCA | 3.546 | 29 |
| UCU | −0.072 | 15 |
| UCC | 6.405 | 32 |
| UCG | −0.502 | 14 |
| UGA | −2.802 | 35 |
| UGU | −1.054 | 30 |
| UGC | 9.247 | 45 |
| UGG | −1.498 | 59 |
| CAA | 2.841 | 31 |
| CAU | 6.933 | 28 |
| CAC | −1.620 | 45 |
| CAG | −4.277 | 35 |
| CUA | 16.112 | 10 |
| CUU | −2.003 | 22 |
| CUC | 1.603 | 30 |
| CUG | −1.000 | 41 |
| CCA | −3.765 | 24 |
| CCU | 5.983 | 31 |
| CCC | −4.530 | 29 |
| CCG | 6.198 | 54 |
| CGA | 5.110 | 34 |
| CGU | −2.940 | 18 |
| CGC | 7.598 | 32 |
| CGG | 5.037 | 49 |
| GAA | 0.859 | 47 |
| GAU | 5.875 | 44 |
| GAC | 1.238 | 31 |
| GAG | −0.134 | 59 |
| GUA | −7.389 | 11 |
| GUU | 5.945 | 16 |
| GUC | 5.753 | 22 |
| GUG | −2.444 | 37 |
| GCA | 9.832 | 45 |
| GCU | 5.189 | 29 |
| GCC | −3.090 | 56 |
| GCG | 4.470 | 40 |
| GGA | 2.845 | 76 |
| GGU | 9.763 | 27 |
| GGC | −0.641 | 55 |
| GGG | −0.194 | 74 |

The P parameters show the significance of various NNN triplets to the antisense inhibitory effect of the sequences in the data set. Negative values mean that some triplets, or combinations of triplets, are actually counterproductive to a maximum antisense effect. One may also note that from the last column in Table 2 that the number of occurrences of the various triplets ranged from 6 to 76 in the sequences used in this database, so all NNN triplets were well represented.

(4) Assess the importance of combinations of the NNN triplets. Table 3 shows the relative importance of the 10 simplest independent combinations of NNN in the target sequences that were analyzed. Because there are constraints linking the NNN, only values for the four triplets that are homopurine or homopyrimidine can be individually determined (three left-hand columns of Table 3). The other 60 triplet values are interrelated and must be expressed as combinations, the simplest of which constitute six repeating sequences ($(CG)_n$, $(AC)_n$, etc.), and these are listed in the three right-hand columns of Table 3. The values in Table 3 reveal that: (a) triplets of RNA purines (GGG, AAA, and AGA+GAG) are all more important than those with RNA pyrimidines (CCC, UUU, and UCU+CUC), consistent with in vitro hybrid oligomer stabilities; (b) GGG is one of the most stable triplets, in agreement with Tu's analysis; (c) AAA also has an unusually high positive effect when it is present in antisense ODNs; and (d) UUU has a negative contribution, in agreement with the well-known instability of rU:dA pairs, which plays an important role in transcription termination in prokaryotes. Overall, the results of this analysis show that such an approach can give parameters pertinent to S-ODN:RNA hybridization in vivo and that results from more extensive data sets will lead to new insights regarding mRNA target selection.

TABLE 3

Values for 10 independent NNN triplets and independent combinations of NNN triplets from an SVD solution to fit the inhibitory data for 102 antisense sequences targeted to four gene mRNAs in two cell lines.

| Independent Triplets | Antisense Inhibitory Parameter | Number of NNN Triplet in Data Set | Six Independent Combinations of Two NNN Triplets | Antisense Inhibitory Parameter | Avg Number of Two NNN Triplets |
|---|---|---|---|---|---|
| AAA | 8.323 | 25 | CGC + GCG | 6.034 | 36.0 |
| GGG | −0.194 | 74 | AGA + GAG | 1.275 | 47.5 |
| UUU | −3.087 | 22 | UCU + CUC | 0.765 | 22.5 |
| CCC | −4.530 | 29 | UGU + GUG | −1.749 | 33.5 |

TABLE 3-continued

Values for 10 independent NNN triplets and independent combinations of NNN triplets from an SVD solution to fit the inhibitory data for 102 antisense sequences targeted to four gene mRNAs in two cell lines.

| Independent Triplets | Antisense Inhibitory Parameter | Number of NNN Triplet in Data Set | Six Independent Combinations of Two NNN Triplets | Antisense Inhibitory Parameter | Avg Number of Two NNN Triplets |
|---|---|---|---|---|---|
| | | | ACA + CAC | −3.678 | 43.0 |
| | | | AUA + UAU | −5.534 | 15.5 |

(5) Apply the derived NNN values to the prediction of antisense effectiveness of other targeted genes. This procedure simply involves the multiplication of each NNN parameter from Table 2 with the number of occurrence of that NNN in the sequence for which a predicted value is desired. If the NNN values have been derived from sequences that are 20 nucleotides long and a predicted value is desired for sequences that are L nucleotides long where L is not 20, the NNN values should be multiplied by L/20. Examples are in the following section.

WORKING EXAMPLES

Example A

Figure 3A:
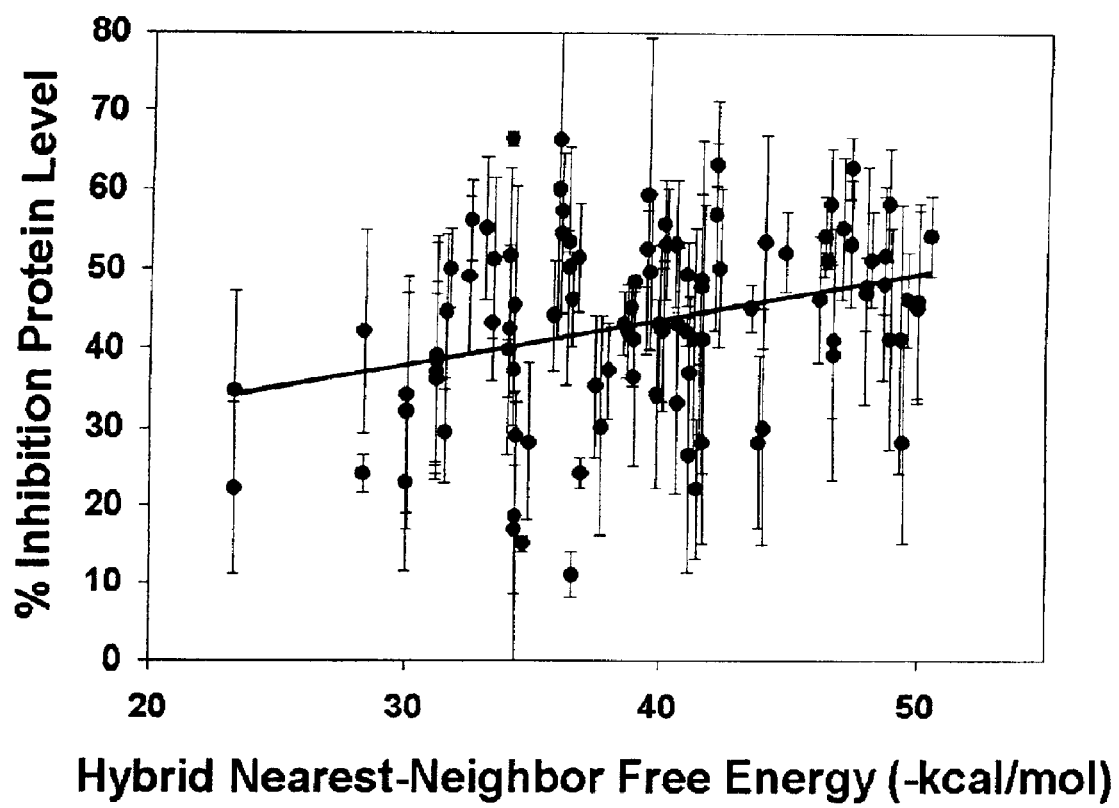
FIG. 3. Graphical illustration of inhibition of protein levels of four gene products in 102 antisense DNA experiments versus (A) levels predicted by in vitro nearest-neighbor parameters and (B) levels predicted by in vivo next-nearest-neighbor parameters. Error bars are +/− one standard deviation.
Figure 3B:
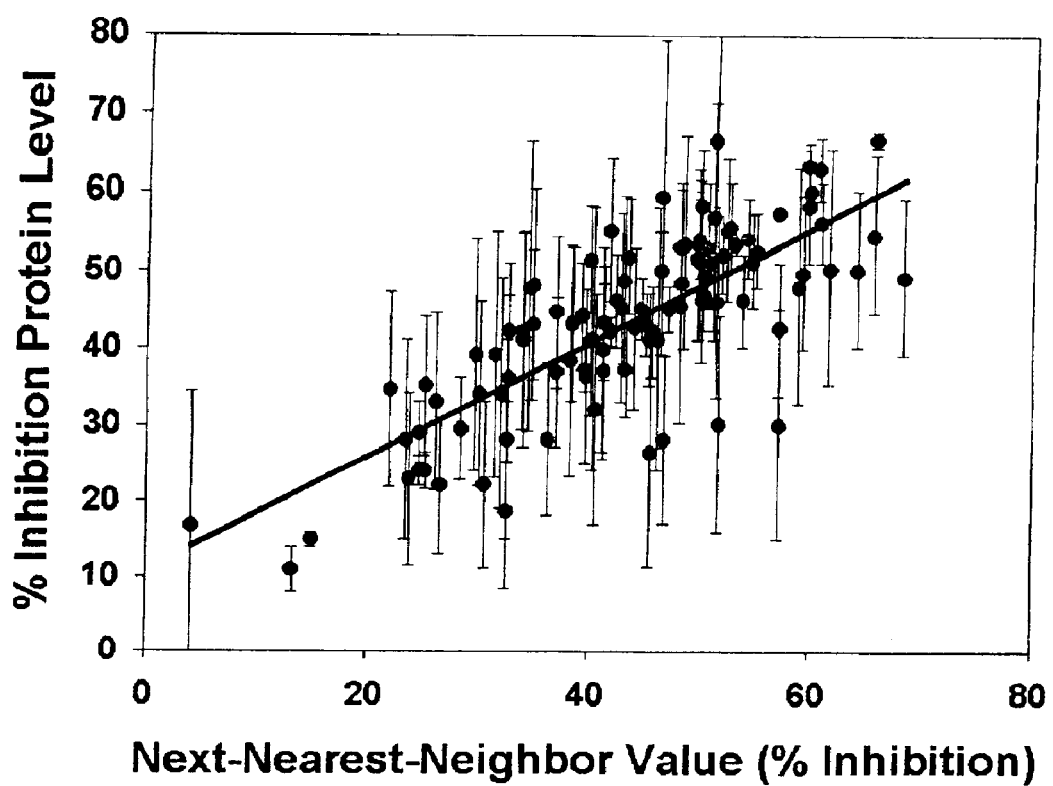

FIG. 3A shows the fit of hybrid NN free energy values, $\Delta G°(37° C.)$, typical of NN stability predictions, to the measured inhibition values for the 102 antisense ODN sequences used to inhibit four gene products in two cell lines (data from Table 1). FIG. 3B shows the fit of the derived NNN values in Table 2, multiplied by the NNN triplets in each of the 102 ODN sequences, to the measured inhibition values. The fit to the NNN data set is better, as is shown by the correlation coefficients, r, and the significance values from the t-text, P, in the first row in Table 4. That is, the NN fit has a regression coefficient of 0.309, while the NNN fit gives a better regression coefficient of 0.778, and a lower value of P, although both fits are significant (below the P=0.05 level).

Example B

Figure 4A:
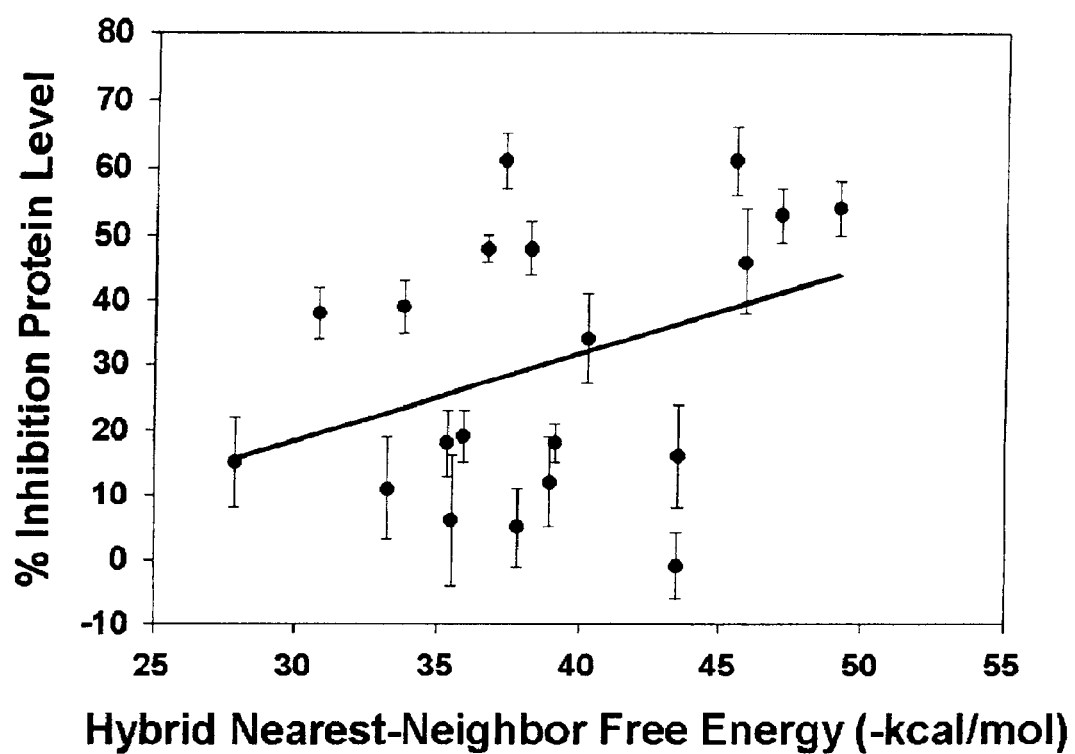
FIG. 4. Graphical illustration of inhibition of PKCα protein levels in 20 antisense DNA experiments (Dean et al., 1994); Western blot assay for loss in protein level versus (A) levels predicted by in vitro nearest-neighbor parameters and (B) levels predicted by in vivo next-nearest-neighbor parameters. Error bars are +/− one standard deviation.
Figure 4B:
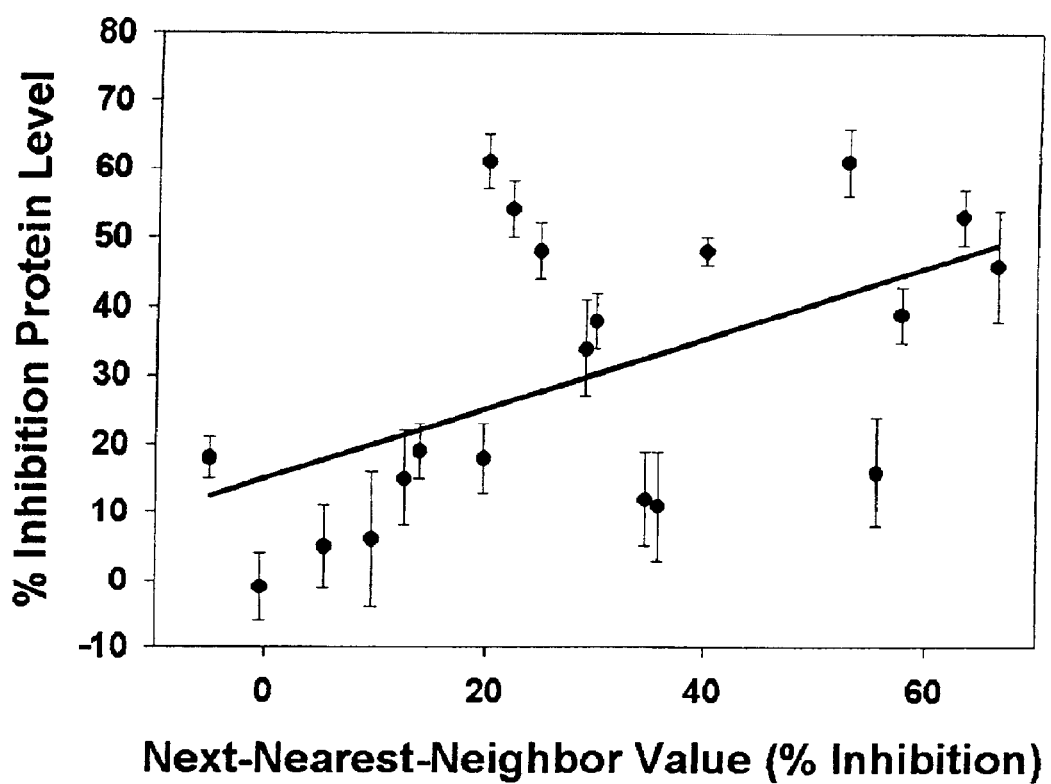

In this example, the predictions from the NNN parameters are compared with those from the NN free energy $\Delta G°$ for a data set that was not used in deriving the NNN parameters of Table 2. The data are published inhibition data from Western blots of PKCα protein taken after treatments with 20 antisense S-ODNs (Dean et al., 1994). As shown in FIGS. 4A and 4B, and in the second line of data in Table 4, the experimental inhibition data are better approximated by those of the in vivo NNN values than by the in vitro NN parameters. It is noteworthy that the NNN parameters give a fit that is significant (P=0.015), while the NN parameters give a fit that is not significant at the P=0.05 level (P=0.110).

Example C

Figure 5A:
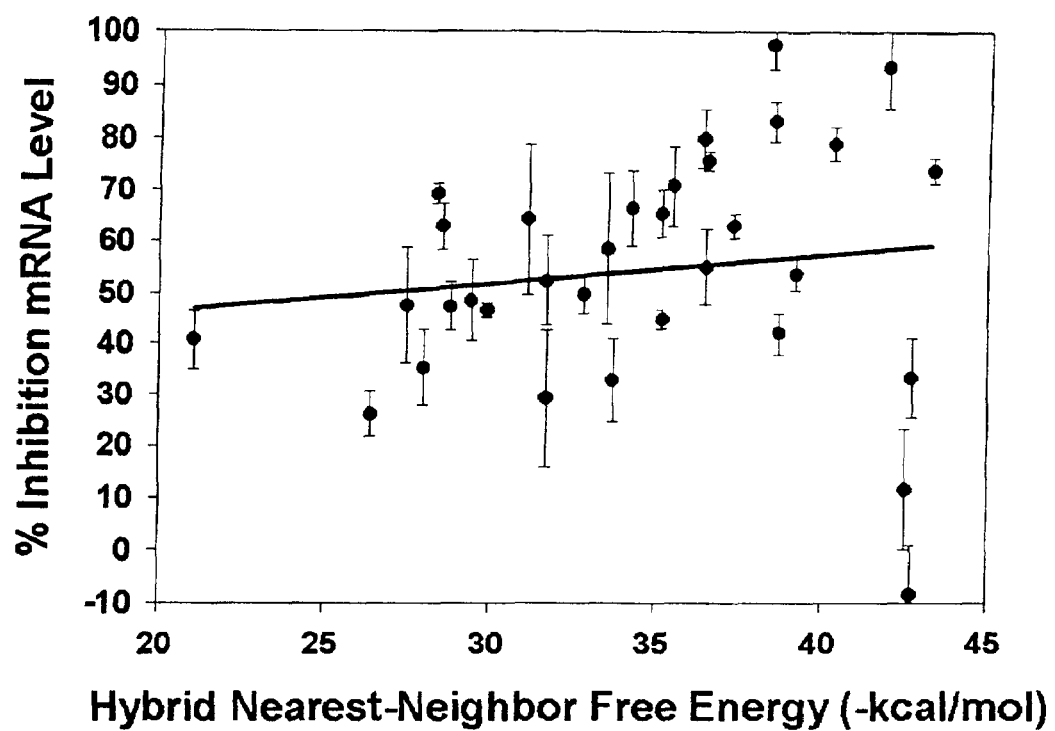
FIG. 5. Graphical illustration of inhibition of adhesion molecule mRNA levels in 33 antisense DNA experiments (Bennett et al., 1994; Northern blot assay for loss in mRNA level) versus (A) levels predicted by in vitro nearest-neighbor parameters and (B) levels predicted by in vivo next-nearest-neighbor parameters. Error bars are +/− one standard deviation.
Figure 5B:
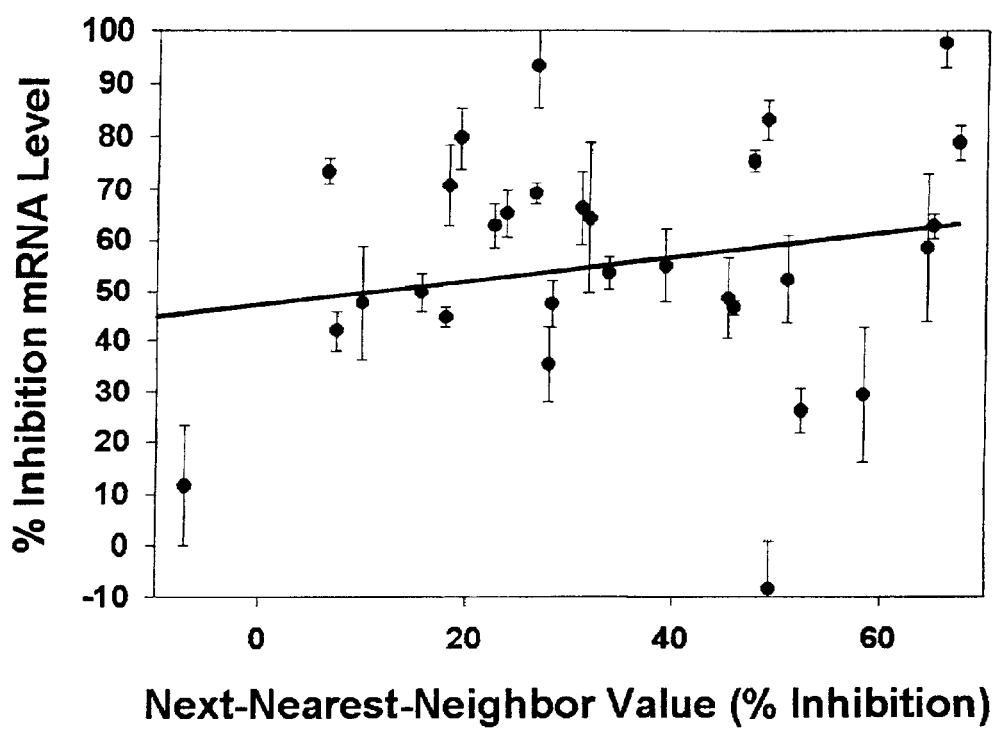
Figure 6A:
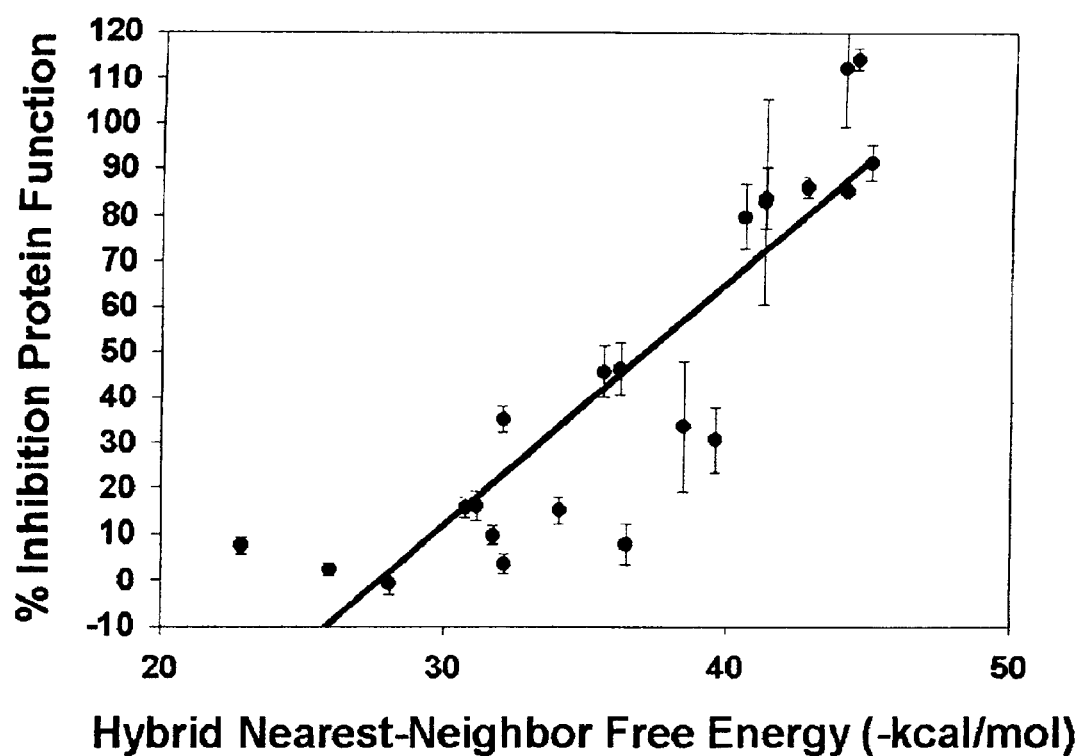
FIG. 6. Graphical illustration of inhibition of P-glycoprotein function in 22 antisense DNA experiments (Ho et al., 1996; rhodamine flux assay) versus (A) levels predicted by in vitro nearest-neighbor parameters and (B) levels predicted by in vivo next-nearest-neighbor parameters. Error bars are +/− one standard deviation.
Figure 6B:
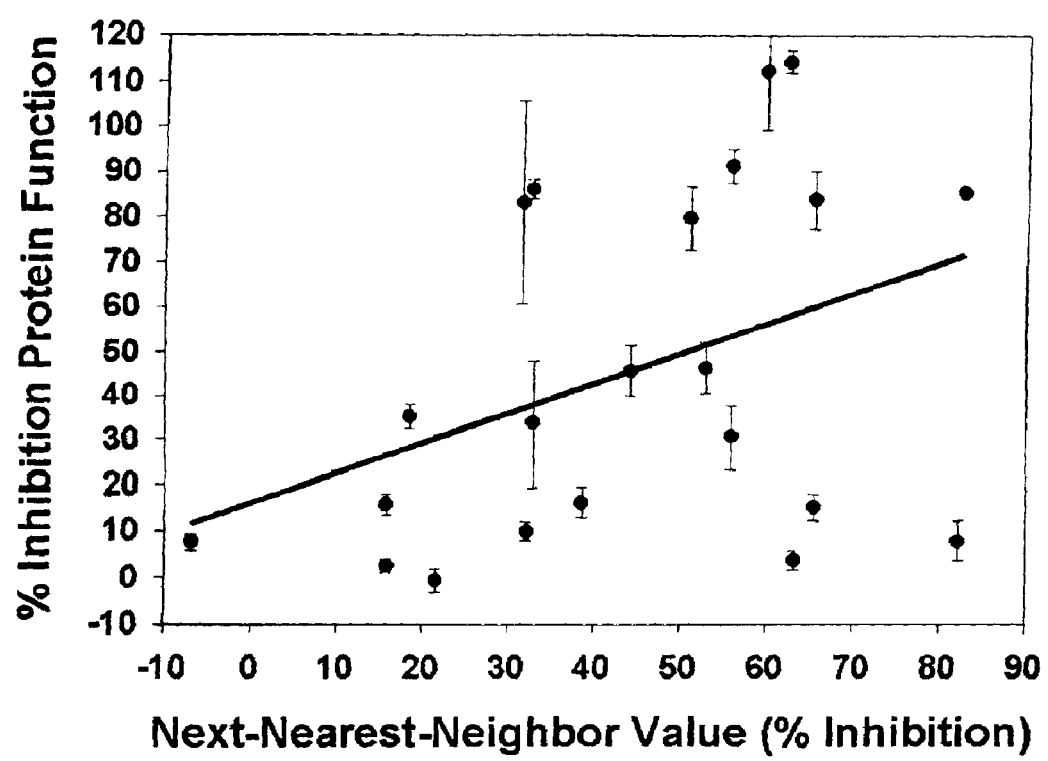

In this example, the predictions from the NNN parameters are compared with those from the NN free energy $\Delta G°$ for a second data set that was not used in deriving the NNN parameters of Table 2. The data are published inhibition data from Northern blots for two adhesion molecule mRNAs (E-Selectin and ICAM-1) taken after treatments with 33 antisense S-ODNs (Bennett et al., 1994). As shown in FIGS. 5A and 5B, and in the third line of data in Table 4, this experimental inhibition data is also better approximated by those of the in vivo NNN values than by the in vitro NN parameters. However, in neither case is the P value below the desired 0.05 value, indicating that additional factors remain to be identified by using a larger data set.

TABLE 4

Comparison of the regression coefficients, r, and the t-test P significance values from fits of various data sets with NN free energy values and with NNN parameters (Table 2).

| Measured data and calculation being compared | Number of sequences | Fit with Nearest-Neighbor Parameters* | | Fit with Next-Nearest-Neighbor Parameters* | |
|---|---|---|---|---|---|
| | | $r_{NN}$ | $P_{NN}$ | $r_{NNN}$ | $P_{NNN}$ |
| 102 sequences from Table 1 | 102 | 0.309 | >0.002 | 0.778 | <0.0001 |
| Published PKC alpha data (Dean et al., 1994) | 20 | 0.368 | 0.110 | 0.536 | 0.015 |
| Published adhesion molecules (Bennett et al., 1994) | 33 | 0.134 | 0.457 | 0.267 | 0.133 |
| Published P-glycoprotein data (Ho et al., 1996) | 22 | 0.879 | <0.0001 | 0.396 | 0.068 |

*r is the coefficient of correlation and P is the significance of r using the t-test. The smaller the value of P the more significant the correlation; P is the level at which the null hypothesis can be rejected.

Example D

In this example, the predictions from the NNN parameters are compared with those from the NN free energy $\Delta G°$ for a fourth data set that was not used in deriving the NNN parameters of Table 2. The data are published inhibition data from inhibition of P-glycoprotein function in 22 antisense DNA experiments using a rhodamine flux assays (Ho et al., 1996). In this case, as may be seen in FIGS. 5A and 5B, and in the last line of data in Table 4, the experimental inhibition data are better approximated by those of the in vitro NN parameters ($P<0.05$), although the in vivo NNN parameters give a fit with $P=0.068$, close to the desired $P=0.05$ level. The ODN sequences used in this study were preselected by an in vitro library of oligonucleotides to test for RNase H sensitive sites. This case serves to illustrate that the NNN methodology differs from methods based on NN stabilities of DNA:mRNA hybrids and is sensitive to different factors during in vivo antisense treatments.

Comparison with other Methodologies

Prior art in identifying effective antisense sequence combinations may be divided into two categories. In the first category, the majority of predictive routines are based on the knowledge that the thermodynamic properties of nucleic acid duplexes reside in the interactions of neighboring bases or base pairs, called nearest-neighbor (NN) properties. The predictive algorithms provided in computer programs including Gray & Clark, 1999; Gray & Clark, 2001, HYB-simulator™ software (RNAture, Inc; Mitsuhashi et al., 1994), OligoWalk (Mathews et al., 1999), a recent program by Walton et al. (2002) and all similar programs, to the knowledge of the inventor, rely on NN properties of nucleic acid duplexes, sometimes augmented with other factors such as changes in the folding of the target mRNA sequence. There are only 13 independent combinations of NN properties in closed sequences. The present invention differs in that it relies on NNN triplet properties of sequences. There are 49 independent NNN triplet combinations for closed sequences. In the second category, researchers have searched for motifs of three or more nucleotides that are present in effective antisense molecules (Tu et al., 1998; Matveeva et al., 2000). The results of such searches do not, however, show how to optimize motif combinations in a given target sequence. Nor do such results allow one to objectively rank the antisense effectiveness of all sequences regardless of differences in their motif combinations. In fact, the theory of nucleotide sequence combinations (Gray 1997a; 1997b) shows that motifs cannot be combined in all combinations. The present invention allows for the derivation of a minimal set of 64 parameters for 64 NNN triplets that can be used to assign parameters for up to 49 independent NNN triplet combinations (i.e. motifs). Values such as those in Table 2 above are sufficient to account for all NNN triplet combinations (i.e. motifs) needed to unambiguously rank the effectiveness of any nucleotide sequence, as long as the sequence is long enough to be considered a closed, circular sequence.

To those knowledgeable in the art, the present method may be expanded to derive 49 NNN combinations from any database with at least 49 sequences for closed sequences. The method may be expanded to cover sequences that are not closed and to derive next-next-nearest-neighbor (NNNN) quadruplet properties.

Bibliography

The following references are hereby specifically incorporated herein by reference:

Basu, S., & E. Wickstrom (1997) *Nucl. Acids Res.* 25, 1327–1332.

Beltinger, C., H. Saragovi, R. Smith, L LeSauteur, N. Shah, L. DeDionisio, L. Christensen, A. Raible, L. Jarett, & A. Gewirtz (1995) *J. Clin. Invest.* 95, 1814–1823.

Bennett, C. F., T. P. Condon, S. Grimm, H. Chan, & M.-Y. Chiang (1994) *J. Immun.* 152, 3530–3540.

Bernstein, P. (1998) *Nature Biotechnology "In Brief"* 16, 10.

Braasch, D. A., & D. R. Corey (2002) *Biochemistry* 41, 4503–4510.

Branch, A. D. (1998) *Trends Biochem. Sci.* 23, 45–50.

Cioffi, C. L., M. Garay, J. F. Johnston, K. McGraw, R. T. Boggs, D. Hreniuk, & B. P. Monia (1997) *Mol. Pharm.* 51, 383–389.

Dean, N. M., R. McKay, T. P. Condon, & C. F. Bennett (1994) *J. Biol. Chem.* 269, 16416–16424.

Eckstein, F. (1998) *Nature Biotechnology "In Brief"* 16, 24.

Eckstein, F. (2000) *Antisense & Nucleic Acid Drug Development* 10, 117–121.

Giles, R. V., D. G. Spiller, J. Grzybowski, R. E. Clark, P. Nicklin, & D. M. Todd (1998) *Nucl. Acids Res.* 26, 1567–1575.

Gray, D. M. (1997a) *Biopolymers*, 42, 783–793.

Gray, D. M. (1997b) *Biopolymers*, 42, 795–810.

Gray, D. M., and C. L. Clark (1999) "Method for Selectively Ranking Sequences for Antisense Targeting" U.S. Pat. No. 5,856,103 issued Jan. 5, 1999.

Gray, D. M., and C. L. Clark (2001) "An Apparatus and Method for Selectively Ranking Sequences for Antisense Targeting" U.S. Pat. No. 6,183,966B1 issued Feb. 6, 2001.

Gray, G. D., S. Basu, & E. Wickstrom (1997) *Biochem. Pharm.* 53, 1465–1476.

Hashem, G. H., J. Pham, M. R. Vaughan, & D. M. Gray (1998) *Biochemistry*, 37, 61–72.

Ho, S. P., D. H. O. Britton, B. A. Stone, D. L. Behrens, L. M. Leffet, F. W. Hobbs, J. A. Miller, & G. L. Trainor (1996) *Nucl. Acids Res.* 24, 1901–1907.

Ho, S. P., Y. Bao, T. Lesher, R. Malhotra, L. Y. Ma., S. J. Fluharty, & R. R. Sakai (1998) *Nat. Biotech.* 16, 59–63.

Hung, S.-H., Q. Yu, D. M. Gray, & R. L. Ratliff (1994) *Nucl. Acids Res.* 22, 4326–4334.

Lesnik, E. A., & S. M. Freier (1995) *Biochemistry* 34, 10807–10815.

Mathews, D. H., M. E. Burkard, S. M. Freier, J. R. Wyatt, & D. H. Turner (1999) *RNA* 5, 1458–1569.

Matveeva, O., B. Felden, A. Tsodikov, J. Johnston, B. P. Monia, J. F. Atkins, R. F. Gesteland, & S. M. Freier (1998) *Nat. Biotech.* 16, 1374–1375.

Matveeva, O. V., A. D. Tsodikov, M. Giddings, S. M. Freier, J. R. Wyatt, A. N. Spiridonov, S. A. Shabalina, R. F. Gesteland, & J. F. Atkins (2000) *Nucl. Acids Res* 28, 2862–2865.

Mercola, D, & Cohen J. S. (1995) *Cancer Gene Ther.* 2, 47–59.

Mitsuhashi, M., Cooper, A., Ogura, M., Shinagawa, T., Yano, K., & Hosokawa, T. (1994) *Nature* 367, 759–761.

Monia, B. P., E. A. Lesnik, C. Gonzalez, W. F. Lima, D. McGee, C. J. Guinosso, A. M. Kawasaki, P. D. Cook, & S. M. Freier (1993) *J. Biol. Chem.* 268, 14514–14522.

Orr, R. M., & B. P. Monia (1998) *Curr. Res. Mol. Therapeutics* 1, 102–108.

Press, W. H., S. A. Teukolsky, W. T. Vetterling, & B. P. Flannery (1992) *Numerical recipes in C, 2nd ed.*, Cambridge University Press, NY, pp. 59–70.

Roberts, R. W., & D. M. Crothers (1992) *Science* 258, 1463–1466.

Sokol, D. L, X. Zhang, P. Lu, A. M. Gewirtz (1998) *Proc. Natl. Acad. Sci. USA* 95, 11538–11543.

Sokol, D. L., & A. M. Gewirtz (1999) *Methods: Companion Meth. Enzymol.* 17, 219–230.

Stein, C., & Y. Cheng (1993) *Science* 261, 1004–1012.

Stein, C. A. (1999) *Nat. Biotech.* 17, 209.

Stull, R. A., L. A. Taylor, & F. C. Szoka, Jr. (1992) *Nucl. Acids Res.* 20, 3501–3508.

Sugimoto, N., S. Nakano, M. Katoh, A. Matsumura, H. Nakamuta, T. Ohmichi, M. Yoneyama, & M. Sasaki (1995) *Biochemistry* 34, 11211–11216.

Tu, G.-C., Q.-N. Cao, F. Zhou, & Y. Israel (1998) *J. Biol. Chem.* 273, 25125–25131.

Wagner, R., & W. Flanagan (1997) *Mol. Med. Today* 3, 31–38.

Walton, S. P., G. N. Stephanopoulos, M. L. Yarmush, & C. M. Roth (2002) *Biophysical J.* 82, 366–377.

and one column for each of the possible M=64 types of next-nearest-neighbor nucleotide triplets for symbolic sequences containing the common four nucleotides, A, U, G, and C, wherein the numbers in the matrix columns are the numbers of each type of next-nearest-neighbor nucleotide triplet in the sequence in the given row;

(b) constructing a matrix Y with N rows and 1 column, wherein the numbers in the rows are measured values corresponding to the biological antisense effectiveness of the N symbolic sequences;

(c) dividing the rows of matrices X and Y by the respective errors in the measured values;

(d) constructing a matrix P having M rows and 1 column, wherein the elements in the rows are variables representing the 64 parameters of antisense effectiveness assigned to the next-nearest-neighbor nucleotide triplets;

What is claimed is:

1. A method for assigning parameters of antisense effectiveness to 64 next-nearest-neighbor nucleotide triplets from measurements of the antisense effectiveness of at least 64 nucleotide sequences, wherein the sequences are considered to be closed sequences without end effects comprising:

(a) constructing a matrix X having N rows and M columns, wherein said matrix X has one row for each of a minimum of N=64 nucleotide symbolic sequences (e) solving equation X multiplied by P equals Y via the singular value decomposition method, wherein said equation is solved for P;

(f) assigning P values as parameters of antisense effectiveness to next-nearest neighbor nucleotide triplets; and (g) displaying antisense effectiveness parameters.

2. The method of claim 1, wherein said measurements of antisense effectiveness are taken from a database of in vitro measurements.

3. The method of claim 1, wherein said measurements of antisense effectiveness are taken from a database of in vivo measurements.

4. The method of claim 1, wherein said measurements of antisense effectiveness are taken from a database of antisense effects with chemical sequences of phosphorothioate oligonucleotides.

5. method of claim 1, wherein said measurements of antisense effectiveness are taken from a database of antisense effectiveness with sequences of chemical moieties that pair with an mRNA sequence in complementary fashion.

6. The method of claim 1, wherein said parameters for said 64 next-nearest-neighbor nucleotide triplets are effective in determining the antisense effectiveness of a phosphorothioate oligonucleotide of about 20 nucleotides in length.

7. The method of claim 6, wherein said parameters for said 64 next-nearest-neighbor nucleotide triplets are multiplied by L/20 for an oligonucleotide which is L nucleotides long.

8. The method of claim 1, wherein said parameters for said 64 next-nearest-neighbor nucleotide triplets are effective in determining the antisense effectiveness of sequences of chemical moieties that pair with an mRNA sequence in complementary fashion for a length of about 20 nucleotides.

9. The method of claim 8, wherein said parameters for said 64 next-nearest-neighbor nucleotide triplets are multiplied by L/20 for an oligonucleotide which is L nucleotides long.

10. The method of claim 1, wherein said parameters for said 64 next-nearest-neighbor nucleotide triplets are combined to give parameters for 49 independent combinations of next-nearest-neighbor nucleotide triplets.

11. The method of claim 1, wherein additional parameters are to be included to specify type of organism, type of cell line, type of gene mRNA, or type of chemically-modified oligomer.

12. A method for assigning parameters to 49 combinations of next-nearest-neighbor nucleotide triplets from measurements of antisense effectiveness of at least 49 sequences, wherein the sequences are considered to be closed sequences without end effects comprising:

(a) constructing a matrix X having N rows and M columns, wherein said matrix X has one row for each of a minimum of N=49 nucleotide symbolic sequences and there is one column for each of the possible M=49 independent combinations of next-nearest-neighbor nucleotide triplets for symbolic sequences containing the common four nucleotides A, U, G, and C, wherein the numbers in the matrix columns are the numbers of each type of independent next-nearest-neighbor nucleotide combination in the sequence in the given row;

(b) constructing a matrix Y having N rows and 1 column, wherein the numbers in the rows are the measured values corresponding to the biological antisense effectiveness of the N symbolic sequences;

(c) dividing the rows of matrices X and Y by the respective errors in the measured values;

(d) constructing a matrix P having M rows and 1 column, wherein the elements in the rows are variables representing the 49 parameters of antisense effectiveness assigned to the next-nearest-neighbor nucleotide triplets;

(e) solving the equation X multiplied by P equals Y via the singular value decomposition method, wherein said equation is solved for P;

(f) assigning P values as parameters of antisense effectiveness to next-nearest neighbor nucleotide triplets; and (g) displaying antisense effectiveness parameters.

13. The method of claim 12, wherein said measurements of antisense effectiveness are taken from a database of in vitro measurements.

14. The method of claim 12, wherein said measurements of antisense effectiveness are taken from a database of in vivo measurements.

15. The method of claim 12, wherein said measurements of antisense effectiveness are taken from a database of antisense effects with chemical sequences of phosphorothioate oligonucleotides.

16. The method of claim 12, wherein said measurements of antisense effectiveness are taken from a database of antisense effectiveness with sequences of chemical moieties that pair with an mRNA sequence in complementary fashion.

17. The method of claim 12, wherein said parameters for said 49 combinations of next-nearest-neighbor nucleotide triplets are effective in determining the antisense effectiveness of a phosphorothioate oligonucleotide of about 20 nucleotides in length.

18. The method of claim 17, wherein said parameters for said 49 combinations of next-nearest-neighbor nucleotide triplets are multiplied by L/20 for an oligonucleotide which is L nucleotides long.

19. The method of claim 12, wherein said parameters for said 49 combinations of next-nearest-neighbor nucleotide triplets are effective in determining the antisense effectiveness of sequences of chemical moieties that pair with an mRNA sequence in complementary fashion for a length of about 20 nucleotides.

20. The method of claim 19, wherein said parameters for said 49 combinations of next-nearest-neighbor nucleotide triplets are multiplied by L/20 for an oligonucleotide which is L nucleotides long.

21. The method of claim 12, wherein additional parameters are to be included to specify type of organism, type of cell line, type of gene mRNA, or type of chemically-modified oligomer.

* * * * *